(12) United States Patent
Ashmore et al.

(10) Patent No.: US 7,951,792 B2
(45) Date of Patent: May 31, 2011

(54) ANTIMICROBIAL COMPOSITION USEFUL FOR PRESERVING WOOD

(75) Inventors: John W. Ashmore, Lansdale, PA (US); Li Liang Chia, Ambler, PA (US); Beverly J. El A'mma, Perkiomenville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1093 days.

(21) Appl. No.: 11/451,494

(22) Filed: Jun. 12, 2006

(65) Prior Publication Data

US 2006/0287288 A1 Dec. 21, 2006

Related U.S. Application Data

(60) Provisional application No. 60/690,685, filed on Jun. 15, 2005.

(51) Int. Cl.
*A61K 31/555* (2006.01)
*A61K 31/325* (2006.01)
*A61K 31/425* (2006.01)

(52) U.S. Cl. ......... 514/184; 514/186; 514/372; 514/479

(58) Field of Classification Search ........................ None
See application file for complete search history.

(56) References Cited

U.S. PATENT DOCUMENTS

| 5,086,048 A | | 2/1992 | Brandes et al. | |
| 5,185,357 A | | 2/1993 | Inui | |
| 5,246,954 A | | 9/1993 | Greiner et al. | |
| 5,527,384 A | * | 6/1996 | Williams et al. | 106/18.32 |
| 5,591,760 A | | 1/1997 | Hsu | |
| 5,827,522 A | * | 10/1998 | Nowak | 424/405 |
| 6,274,199 B1 | * | 8/2001 | Preston et al. | 427/298 |
| 6,676,745 B2 | * | 1/2004 | Merkley et al. | 106/726 |
| 6,767,647 B2 | | 7/2004 | Swofford et al. | |
| 2006/0270758 A1 | * | 11/2006 | Ong et al. | 523/171 |

FOREIGN PATENT DOCUMENTS

| EP | 0431752 | | 6/1991 |
| JP | 48002331 | | 10/1969 |
| JP | 03007205 | | 1/1991 |
| JP | 03200703 | | 9/1991 |
| JP | 04169502 | | 6/1992 |
| JP | 04264011 | | 9/1992 |
| JP | 08-012504 A | | 1/1996 |
| JP | 2001247414 | | 9/2001 |
| JP | 2003095828 | * | 9/2001 |
| JP | 2003095828 | | 4/2003 |
| JP | 2003206205 | | 7/2003 |
| JP | 2003212705 | | 7/2003 |
| JP | 2004099529 | | 4/2004 |
| JP | 2004168678 | | 6/2004 |
| JP | 2006056041 | | 3/2006 |
| WO | WO 01/10217 | | 2/2001 |

OTHER PUBLICATIONS

Derwent English abstract of JP 2003095828 (full citation above).*
Presnell, et al., "Evaluation of Combinations of Low Hazard Biocides in Controlling Mold and Stain Fungi on Southern Pine" J. Forest Product, vol. 40, No. 2, pp. 57-61 (1990).
Yalcin Ors, et al., "Bonding Strength of Some Adhesives in Wood Materials", International Journal of Adhesion & Adhesives, vol. 24, pp. 287-294 (2004).

* cited by examiner

*Primary Examiner* — Shanon A Foley
(74) *Attorney, Agent, or Firm* — Kenneth Crimaldi

(57) ABSTRACT

Antimicrobial compositions useful for preserving wood, and comprising a variety of antimicrobial compounds.

1 Claim, No Drawings

ANTIMICROBIAL COMPOSITION USEFUL FOR PRESERVING WOOD

This is a non-provisional application of prior pending U.S. provisional Application Ser. No. 60/690,685 filed on Jun. 15, 2005.

This invention relates to combinations of biocides useful for preserving wood, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, U.S. Pat. No. 5,591,760 discloses a synergistic combination of 4,5-dichloro-2-n-octyl-4-isothiazolin-3-one and a number of other biocides, including 3-iodo-2-propynyl-butylcarbamate, but this reference does not suggest any of the combinations claimed herein. Moreover, there is a need for additional combinations of antimicrobial compounds having enhanced activity against various strains of microorganisms to provide effective control of the microorganisms that is both quick and long lasting. The problem addressed by this invention is to provide such additional combinations of antimicrobial compounds.

STATEMENT OF THE INVENTION

The present invention is directed to a synergistic antimicrobial composition comprising: (a) 4,5-dichloro-2-n-octyl-4-isothiazolin-3-one; and (b) copper tebuconazole.

The present invention is further directed to a synergistic antimicrobial composition comprising: (a) 4,5-dichloro-2-n-octyl-4-isothiazolin-3-one; and (b) 2-methyl-4-isothiazolin-3-one.

The present invention is further directed to a synergistic antimicrobial composition comprising: (a) a copper alkyldimethylammonium salt; and (b) copper 8-hydroxyquinoline.

The present invention is further directed to a synergistic antimicrobial composition comprising: (a) a copper alkyldimethylammonium salt; and (b) 2-n-octyl-4-isothiazolin-3-one.

The present invention is further directed to a synergistic antimicrobial composition comprising: (a) copper 8-hydroxyquinoline; and (b) 2-n-octyl-4-isothiazolin-3-one.

The present invention is further directed to a synergistic antimicrobial composition comprising: (a) copper 8-hydroxyquinoline; and (b) 3-iodo-2-propynyl-butylcarbamate.

The present invention is further directed to a synergistic antimicrobial composition comprising: (a) tebuconazole; and (b) a microbicide selected from the group consisting of 4,5-dichloro-2-n-octyl-4-isothiazolin-3-one; copper 8-hydroxyquinoline; 2-n-octyl-4-isothiazolin-3-one; and a mixture of 5-chloro-2-methyl-4-isothiazolin-3-one and 2-methyl-4-isothiazolin-3-one.

The present invention is further directed to a synergistic antimicrobial composition comprising: (a) propiconazole; and (b) a microbicide selected from the group consisting of 4,5-dichloro-2-n-octyl-4-isothiazolin-3-one; copper 8-hydroxyquinoline; 2-n-octyl-4-isothiazolin-3-one; a mixture of 5-chloro-2-methyl-4-isothiazolin-3-one and 2-methyl-4-isothiazolin-3-one; and 3-iodo-2-propynyl-butylcarbamate.

The present invention is further directed to a synergistic antimicrobial composition comprising: (a) 4,5-dichloro-2-n-octyl-4-isothiazolin-3-one; and (b) copper 8-hydroxyquinoline.

The present invention is further directed to a synergistic antimicrobial composition comprising: (a) 4,5-dichloro-2-n-octyl-4-isothiazolin-3-one; and (b) thifluzamide.

DETAILED DESCRIPTION OF THE INVENTION

"MI" is 2-methyl-4-isothiazolin-3-one, also referred to by the name 2-methyl-3-isothiazolone. "CMI" is 5-chloro-2-methyl-4-isothiazolin-3-one. "DCOIT" is 4,5-dichloro-2-n-octyl-4-isothiazolin-3-one. "OIT" is 2-n-octyl-4-isothiazolin-3-one. "IPBC" is 3-iodo-2-propynyl-butylcarbamate. Copper tebuconazole is a biocide formulation containing a monoethanolamine complex of copper oxide and tebuconazole.

A "copper alkyldimethylammonium salt" is a biocide formulation containing a monoethanolamine complex of copper oxide and an alkyldimethylammonium salt. In one embodiment, the alkyldimethylammonium salt is alkylbenzyldimethylammonium salt. In another embodiment, the alkyldimethylammonium salt is dialkyldimethylammonium salt. In another embodiment, the alkyldimethylammonium salt is an aryloxyethoxyethyl dimethyl benzylammonium salt, wherein aryl preferably is diisobutylphenyl or diisobutylcresyl. Preferably the salt is a chloride, carbonate or bicarbonate. Preferably, the weight ratio of copper oxide to alkyldimethylammonium salt is from 30:70 to 80:20. In one embodiment, the ratio of copper oxide to alkyldimethylammonium salt is from 55:45 to 80:20, more preferably from 62:38 to 71:29. In another embodiment, the ratio is from 35:65 to 65:35, more preferably from 45:55 to 55:45. Preferably the alkyl groups are in the range from $C_8$-$C_{18}$, with the majority being $C_8$-$C_{14}$. In one embodiment, the alkyl groups are 67% $C_{12}$, 25% $C_{14}$, 7% $C_{16}$ and 1% $C_{18}$. In another embodiment, the alkyl groups are from $C_8$-$C_{12}$.

As used herein, the following terms have the designated definitions, unless the context clearly indicates otherwise. The term "antimicrobial compound" refers to a compound capable of inhibiting the growth of or controlling the growth of microorganisms at a locus; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages (%) are by weight. Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. "Salt-free" means that the composition contains zero or up to 0.5%, preferably zero or up to 0.1%, and more preferably zero or up to 0.01%, of metal salt, based on weight of the composition.

In one embodiment of the invention, the antimicrobial composition comprises 4,5-dichloro-2-n-octyl-4-isothiazolin-3-one and copper tebuconazole. Preferably, a weight ratio of 4,5-dichloro-2-n-octyl-4-isothiazolin-3-one to copper tebuconazole is from 1:400 to 1:6. Another preferred weight ratio is from 1:333 to 1:6.3.

In another embodiment of the invention, the antimicrobial composition comprises 4,5-dichloro-2-n-octyl-4-isothiazolin-3-one and 2-methyl-4-isothiazolin-3-one. Preferably, a weight ratio of 4,5-dichloro-2-n-octyl-4-isothiazolin-3-one to 2-methyl-4-isothiazolin-3-one is from 1:1.4 to 1:1800. Another preferred weight ratio is from 1:1.4 to 1:1750.

In another embodiment of the invention, the antimicrobial composition comprises copper alkyldimethylammonium salt and copper 8-hydroxyquinoline. Preferably, a weight ratio of copper alkyldimethylammonium salt to copper 8-hydroxyquinoline is from 1:0.8 to 1:15. Another preferred weight ratio is from 1:1 to 1:4.

In another embodiment of the invention, the antimicrobial composition comprises copper alkyldimethylammonium salt and 2-n-octyl-4-isothiazolin-3-one. Preferably, a weight ratio of copper alkyldimethylammonium salt to 2-n-octyl-4-isothiazolin-3-one is from 1:0.02 to 1:88. Another preferred weight ratio is from 1:0.02 to 1:87.5, and another from 1:0.02 to 1:60.

In another embodiment of the invention, the antimicrobial composition comprises copper 8-hydroxyquinoline and 2-n-octyl-4-isothiazolin-3-one. Preferably, a weight ratio of copper 8-hydroxyquinoline to 2-n-octyl-4-isothiazolin-3-one is from 1:60 to 1:0.008. Another preferred weight ratio is from 1:59 to 1:0.009, and another from 1:50 to 1:0.009.

In another embodiment of the invention, the antimicrobial composition comprises copper 8-hydroxyquinoline and 3-iodo-2-propynyl-butylcarbamate. Preferably, a weight ratio of copper 8-hydroxyquinoline to 3-iodo-2-propynyl-butylcarbamate is from 1:30 to 1:0.2. Another preferred weight ratio is from 1:23 to 1:0.3.

In another embodiment of the invention, the antimicrobial composition comprises tebuconazole and a microbicide selected from the group consisting of 4,5-dichloro-2-n-octyl-4-isothiazolin-3-one; copper 8-hydroxyquinoline; 2-n-octyl-4-isothiazolin-3-one; and a mixture of 5-chloro-2-methyl-4-isothiazolin-3-one and 2-methyl-4-isothiazolin-3-one. Preferably, a weight ratio of tebuconazole to DCOIT is from 1:0.0003 to 1/0.6. Preferably, a weight ratio of tebuconazole to copper 8-hydroxyquinoline is from 1/0.005 to 1/1.6; another preferred weight ratio is from 1/0.006 to 1/1.58. Preferably, a weight ratio of tebuconazole to OIT is from 1/0.001 to 1/0.3; another preferred weight ratio is from 1/0.002 to 1/0.24. Preferably, a weight ratio of tebuconazole to a mixture of 5-chloro-2-methyl-4-isothiazolin-3-one and 2-methyl-4-isothiazolin-3-one is from 1/0.001 to 1/0.15.

In another embodiment of the invention, the antimicrobial composition comprises propiconazole and a microbicide selected from the group consisting of 4,5-dichloro-2-n-octyl-4-isothiazolin-3-one; copper 8-hydroxyquinoline; 2-n-octyl-4-isothiazolin-3-one; a mixture of 5-chloro-2-methyl-4-isothiazolin-3-one and 2-methyl-4-isothiazolin-3-one; and 3-iodo-2-propynyl-butylcarbamate. Preferably, a weight ratio of propiconazole to DCOIT is from 1/0.002 to 1/0.9; another preferred weight ratio is from 1/0.026 to 1/0.875. Preferably, a weight ratio of propiconazole to copper 8-hydroxyquinoline is from 1/0.02 to 1/1.5; another preferred weight ratio is from 1/0.023 to 1/1.28. Preferably, a weight ratio of propiconazole to OIT is from 1/0.001 to 1/0.5; another preferred weight ratio is from 1/0.0015 to 1/0.48. Preferably, a weight ratio of propiconazole to a mixture of 5-chloro-2-methyl-4-isothiazolin-3-one and 2-methyl-4-isothiazolin-3-one is from 1/0.008 to 1/0.15; another preferred weight ratio is from 1/0.009 to 1/0.12. Preferably, a weight ratio of propiconazole to 3-iodo-2-propynyl-butylcarbamate is from 1/0.0005 to 1/0.015; another preferred weight ratio is from 1/0.0007 to 1/0.011.

In another embodiment of the invention, the antimicrobial composition comprises DCOIT and thifluzamide. Preferably, a weight ratio of DCOIT to thifluzamide is from 1/0.1 to 1/10; another preferred weight ratio is from 1/0.5 to 1/2.

In another embodiment of the invention, the antimicrobial composition comprises copper 8-hydroxyquinoline and DCOIT. Preferably, a weight ratio of copper 8-hydroxyquinoline to DCOIT is from 1/0.002 to 1/0.01; another preferred weight ratio is from 1/0.005 to 1/0.08; and another is from 1/0.005 to 1/0.03.

In one embodiment of the invention, those antimicrobial compositions which contain 2-methyl-4-isothiazolin-3-one (MI) contain relatively low levels of 5-chloro-2-methyl-4-isothiazolin-3-one (CMI), preferably no more than 5%, more preferably no more than 2%, and most preferably no more than 1.2%. Another preferred level is no more than 0.5%, and another is no more than 0.1%. In another embodiment, CMI and MI are present as a mixture in a ratio from 4:1 to 1:1, preferably from 3.5:1 to 2.5:1. A commercial product is available which has a CMI:MI ratio of about 3:1.

The antimicrobial compounds in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, glycerol triacetate, TEXANOL (2,2,4-trimethyl-1,3-pentanediol, mono-isobutyrate ester; available from Eastman Co., Kingsport Tenn.), and methyl and isobutyl esters of $C_3$-$C_7$ dicarboxylic acids, e.g., succinic, glutaric and adipic acids; carbonates, such as propylene carbonate and dimethyl carbonate; and mixtures thereof. It is preferred that the solvent is selected from water, glycols, glycol ethers, esters and mixtures thereof Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When an antimicrobial component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art. U.S. Pat. No. 5,444,078 may be consulted for further general and specific details on the preparation of various microemulsions and microemulsive concentrates.

An antimicrobial compound also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

The antimicrobial compounds may be formulated separately or together. When both antimicrobial compounds are each first formulated with a solvent, the solvent used for the first antimicrobial compound may be the same as or different from the solvent used to formulate the other commercial antimicrobial compound. It is preferred that the two solvents are miscible. In the alternative, the first antimicrobial compound and the other antimicrobial compound may be combined directly and then a solvent added to the mixture.

Those skilled in the art will recognize that the antimicrobial compounds of the present invention may be added to a locus sequentially, simultaneously, or may be combined before being added to the locus. It is preferred that the first antimicrobial compound and the second antimicrobial compound be added to a locus simultaneously or combined prior to being added to the locus. When the antimicrobial compounds are combined prior to being added to a locus, such combination may optionally contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The antimicrobial compositions of the present invention can be used to inhibit the growth of microorganisms by introducing an antimicrobially effective amount of the compositions onto, into, or at a locus subject to microbial attack. Suitable loci include, for example: cooling towers; air washers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the antimicrobial compositions of the present invention are used to inhibit the growth of microorganisms at a locus selected from one or more of wood and wood products, emulsions, dispersions, paints, latices, household products, cosmetics, toiletries, shampoos, soaps, detergents, machining fluids and industrial cleaners. In particular, the antimicrobial compositions are useful in wood and wood products, emulsions, dispersions, paints and latices.

When the synergistic compositions of the present invention are used in personal care compositions, the formulated compositions may also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

The specific amount of the composition of this invention necessary to inhibit or control the growth of microorganisms in a locus depends upon the particular locus to be protected. Typically, the amount of the composition of the present invention to control the growth of microorganisms in a locus is sufficient if it provides from 0.1 to 25,000 ppm active ingredient of the composition in the locus. It is preferred that the active ingredients of the composition be present in the locus in an amount of at least 0.5 ppm, more preferably at least 1 ppm, more preferably at least 10 ppm and most preferably at least 50 ppm. In one embodiment of the invention, the active ingredients are present in an amount of at least 500 ppm. It is preferred that the active ingredients of the composition be present in the locus in an amount of no more than 20,000 ppm, more preferably no more than 15,000 ppm, more preferably no more than 1000 ppm. In one embodiment of the invention, the active ingredients are present in an amount of no more than 10,000 ppm, more preferably no more than 5,000 ppm, and most preferably no more than 1,000 ppm.

EXAMPLES

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$C_a/C_A + C_b/C_B = \text{Synergy Index ("SI")}$$

wherein:
$C_A$=concentration of compound A (first component) in ppm, acting alone, which produced an end point (MIC of Compound A).
$C_a$=concentration of compound A in ppm, in the mixture, which produced an end point.
$C_B$=concentration of compound B (second component) in ppm, acting alone, which produced an end point (MIC of Compound B).
$C_b$=concentration of compound B in ppm, in the mixture, which produced an end point.

When the sum of $C_a/C_A$ and $C_b/C_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of an antimicrobial compound is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for bacteria testing; Potato Dextrose Broth (PDB medium) was used for yeast and mold testing. In this method, a wide range of combinations of microbicides was tested by conducting high resolution MIC assays in the presence of various concentrations of biocides. High resolution MICs were determined by adding varying amounts of microbicide to one column of a microtitre plate and doing subsequent ten-fold dilutions using an automated liquid handling system to obtain a series of end points ranging of active ingredient. The synergy of the combinations of the present invention was determined against two bacteria, *Pseudomonas aeruginosa* (*Ps. aeruginosa*—ATCC #9027) and *Staphylococcus aureus* (*S. aureus*—ATCC #6538), a yeast, *Candida albicans* (*C.* albicans—ATCC #10231), and a mold, *Aspergillus niger* (*A. niger*—ATCC 16404). The bacteria were used at a concentration of about 1-6×10⁶ bacteria per mL and the yeast and mold at 1-5×10⁵ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the microbicide combinations of the present invention are shown below in the Tables. Each table shows the specific combinations of Component (a) and the second component (b); results against the microorganisms tested with incubation times; the end-point activity in ppm measured by the MIC for Component (a) ($C_a$), for the second component alone ($C_b$), for the mixture ($C_a$) and for second component in the mixture ($C_b$); the calculated SI value; and the range of synergistic ratios for each combination tested (first component/second component or a+b).

An application test was performed to evaluate synergy of DCOIT/thifluzamide alone and in combination against *Gloeophyllum trabeum* (*G. trabeum*—ATCC #11593) and *Trametes vesicolor* (*T. vesicolor*—ATCC #4262). A paper disc was dipped in the treatment solution, air dried and placed on Malt agar plate streaked with the test organisms. The surface of the disc was also swabbed with the test organisms. The agar plates were incubated at 25° C. for 4 weeks. Fungal growth was then observed visually.

The following Tables summarize data for combinations of biocides against fungi and bacteria, along with their synergy index (SI) and the weight ratios of biocides. All amounts of biocides are reported as ppm of active ingredient.

| Ca = Component A (ACQ-C)[1] | | | | | |
|---|---|---|---|---|---|
| Cb = Component B (copper 8-hydroxyquinoline) | | | | | |
| Ratio = Ca/Cb | | | | | |
| Test Organisms | Contact Time | Ca | Cb | S.I. | Ca/Cb |
| S. aureus | 48 hour | 2 | — | — | — |
| ATCC # 6538 | | — | 3 | — | — |
| | | 0.53 | 1 | 0.6 | 1/2 |
| | | 0.65 | 1 | 0.66 | 1/1.5 |
| | | 0.88 | 1 | 0.77 | 1/1.4 |
| | | 1.1 | 1 | 0.88 | 1/0.9 |
| | | 0.53 | 2 | 0.93 | 1/4 |
| | | 0.65 | 2 | 0.99 | 1/3 |
| | | 0.88 | 2 | 1.11 | 1/2.3 |
| A. niger | 3 days | 32 | — | — | — |
| ATCC # 16404 | | — | 7 | — | — |
| | | 6.6 | 5 | 0.92 | 1/0.8 |
| | 7 days | 32 | — | — | — |
| | | — | 8 | — | — |
| | | 6.6 | 6 | 0.96 | 1/0.9 |
| C. albicans | 24 hour | 4.6 | — | — | — |
| ATCC # 10231 | | — | 15 | — | — |
| | | 2.1 | 5 | 0.79 | 1/2.4 |
| | | 3 | 5 | 0.99 | 1/1.7 |
| | | 0.8 | 10 | 0.84 | 1/12.5 |
| | | 1.4 | 10 | 0.97 | 1/7.1 |
| | 48 hour | 6.1 | — | — | — |
| | | — | 20 | — | — |
| | | 2.1 | 5 | 0.59 | 1/2.4 |
| | | 3 | 5 | 0.74 | 1/1.7 |
| | | 4.6 | 5 | 1 | 1/1.1 |
| | | 1.4 | 15 | 0.98 | 1/10.7 |

[1]"ACQ-C" is a formulation of copper oxide monoethanolamine complex with alkyl benzyldimethylammonium chloride, wherein the alkyl group is a mixture of $C_8$-$C_{18}$ alkyls, with the majority being $C_{12}$ and $C_{14}$, and the weight ratio of copper oxide to alkyl benzyldimethylammonium chloride is from 62:38 to 71:29.

| Ca = Component A (DCOIT) | | | | | |
|---|---|---|---|---|---|
| Cb = Component B (MI) | | | | | |
| Ratio = Ca/Cb | | | | | |
| Test Organisms | Contact Time | Ca | Cb | S.I. | Ca/Cb |
| Ps. Aeruginosa | 24 hour | 3.2 | — | — | — |
| ATCC # 9027 | | — | 20 | — | — |
| | | 0.7 | 15 | 0.97 | 1/21.5 |
| | 48 hour | 5.3 | — | — | — |
| | | — | 20 | — | — |
| | | 3.9 | 5 | 0.99 | 1/1.3 |
| | | 2.6 | 10 | 0.99 | 1/3.8 |
| | | 1.8 | 10 | 0.84 | 1/5.6 |
| | | 1.2 | 15 | 0.98 | 1/12.5 |
| | | 1.8 | 15 | 1.09 | 1/8.3 |
| | | 3.2 | 10 | 1.1 | 1/3.1 |
| S. aureus | 24 hour | 0.1 | — | — | — |
| ATCC #6538 | | — | 30 | — | — |
| | | 0.04 | 20 | 1.07 | 0 |
| | 48 hour | 0.4 | — | — | — |
| | | — | 40 | — | — |
| | | 0.1 | 25 | 0.88 | 1/250 |
| | | 0.04 | 30 | 0.85 | 1/750 |
| | | 0.06 | 30 | 0.9 | 1/500 |
| | | 0.1 | 30 | 1 | 1/300 |
| A. niger | 3 days | 1 | — | — | — |
| ATCC # 16404 | | — | 450 | — | — |
| | | 0.55 | 200 | 0.99 | 2/727 |
| | | 0.44 | 250 | 1 | 1/568 |
| | | 0.26 | 300 | 0.93 | 1/1153 |
| | | 0.33 | 300 | 1 | 1/909 |
| | | 0.26 | 350 | 1.04 | 1/1346 |
| | 7 days | 1 | — | — | — |
| | | — | 450 | — | — |
| | | 0.3 | 300 | 0.97 | 1/1000 |

| Ca = Component A (copper 8-hydroxyquinoline) | | | | | |
|---|---|---|---|---|---|
| Cb = Component B (OIT) | | | | | |
| Ratio = Ca/Cb | | | | | |
| Test Organisms | Contact Time | Ca | Cb | S.I. | Ca/Cb |
| Ps. Aeruginosa | 48 hour | 7 | — | — | — |
| ATCC # 9027 | | — | 415 | — | — |
| | | 3 | 180 | 0.86 | 1/60 |
| | | 3 | 255 | 1.04 | 1/85 |
| S. aureus | 24 hour | 3 | — | — | — |
| ATCC # 6538 | | — | 63 | — | — |
| | | 1 | 36 | 0.9 | 1/36 |
| | | 2 | 13.2 | 0.88 | 1/6.6 |
| | | 2 | 24 | 1.05 | 1/12 |
| | 48 hour | 4 | — | — | — |
| | | — | 78 | — | — |
| | | 1 | 51 | 0.9 | 1/51 |
| | | 1 | 63 | 1.06 | 1/63 |
| | | 2 | 36 | 0.96 | 1/18 |
| | | 3 | 13.2 | 0.92 | 1/4.4 |
| C. albicans | 24 hour | 15 | — | — | — |
| ATCC # 10231 | | — | 0.6 | — | — |
| | | 5 | 0.33 | 0.88 | 1/0.06 |
| | | 10 | 0.09 | 0.82 | 1/0.01 |
| | | 10 | 0.13 | 0.88 | 1/0.01 |
| | | 10 | 0.16 | 0.93 | 1/0.02 |
| | | 10 | 0.2 | 1 | 1/0.02 |
| | 48 hour | 15 | — | — | — |
| | | — | 0.9 | — | — |
| | | 10 | 0.2 | 0.89 | 1/0.02 |
| | | 10 | 0.26 | 0.96 | 1/0.03 |
| | | 5 | 0.6 | 1 | 1/0.02 |

| Ca = Component A (ACQ-C) Cb = Component B (OIT) Ratio = Ca/Cb | | | | | |
|---|---|---|---|---|---|
| Test Organisms | Contact Time | Ca | Cb | S.I. | Ca/Cb |
| *Ps. Aeruginosa* ATCC # 9027 | 24 hour | 20 | — | — | — |
| | | — | 390 | — | — |
| | | 5 | 315 | 1.06 | 1/63 |
| | | 15 | 129 | 1.06 | 1/8.6 |
| | 48 hour | 20 | — | — | — |
| | | — | 525 | — | — |
| | | 10 | 255 | 0.99 | 1/25.5 |
| | | 15 | 180 | 1.09 | 1/12 |
| *S. aureus* ATCC # 6538 | 24 hour | 1 | — | — | — |
| | | — | 63 | — | — |
| | | 0.4 | 24 | 0.78 | 1/60 |
| | | 0.6 | 24 | 0.98 | 1/40 |
| | | 0.4 | 36 | 0.97 | 1/90 |
| | | 0.6 | 10.5 | 0.77 | 1/17.5 |
| | | 0.8 | 10.5 | 0.97 | 1/13.1 |
| | 48 hour | 2 | — | — | — |
| | | — | 78 | — | — |
| | | 0.8 | 51 | 1.05 | 1/63.8 |
| *C. albicans* ATCC # 10231 | 24 hour | 8 | — | — | — |
| | | — | 0.6 | — | — |
| | | 2 | 0.3 | 0.75 | 1/0.15 |
| | | 4 | 0.3 | 1 | 1/0.08 |
| | 48 hour | 8 | — | — | — |
| | | — | 0.9 | — | — |
| | | 2 | 0.6 | 0.92 | 1/0.3 |
| *A. niger* ATCC # 16404 | 3 days | 30 | — | — | — |
| | | — | 3.3 | — | — |
| | | 5 | 1 | 0.47 | 1/0.2 |
| | | 5 | 1.5 | 0.62 | 1/0.3 |
| | | 5 | 2.1 | 0.8 | 1/0.4 |
| | | 5 | 2.6 | 0.95 | 1/0.5 |
| | | 10 | 0.33 | 0.43 | 1/0.03 |
| | | 10 | 0.44 | 0.47 | 1/0.04 |
| | | 10 | 0.55 | 0.5 | 1/0.06 |
| | | 10 | 1 | 0.64 | 1/0.1 |
| | | 20 | 0.33 | 0.77 | 1/0.017 |
| | 7 days | 30 | — | — | — |
| | | — | 3.3 | — | — |
| | | 10 | 1 | 0.64 | 1/0.1 |
| | | 10 | 1.5 | 0.79 | 1/0.15 |
| | | 10 | 2.1 | 0.97 | 1/0.21 |
| | | 20 | 1 | 0.97 | 1/0.05 |

| Ca = Component A (copper 8-hydroxyquinoline) Cb = Component B (IPBC) Ratio = Ca/Cb | | | | | |
|---|---|---|---|---|---|
| Test Organisms | Contact Time | Ca | Cb | S.I. | Ca/Cb |
| *Ps. Aeruginosa* ATCC # 9027 | 24 hour | 7 | — | — | — |
| | | — | 263 | — | — |
| | | 2 | 195 | 1.03 | 1/97.5 |
| | | 3 | 158 | 1.03 | 1/52.7 |
| | | 4 | 60 | 0.8 | 1/15 |
| | | 4 | 90 | 0.91 | 1/22.5 |
| | | 5 | 60 | 0.94 | 1/12 |
| | 48 hour | 7 | — | — | — |
| | | — | 263 | — | — |
| | | 3 | 128 | 0.92 | 1/42.7 |
| | | 3 | 158 | 1.03 | 1/52.7 |
| | | 4 | 128 | 1.06 | 1/32 |
| *S. aureus* ATCC # 6538 | 24 hour | 3 | — | — | — |
| | | — | 34 | — | — |
| | | 1 | 8.8 | 0.59 | 1/8.8 |
| | | 1 | 16 | — | 1/16 |
| | | 2 | 24 | 1.04 | 1/24 |
| | | 2 | 8.8 | 0.93 | 1/4.4 |
| | | 2 | 4.2 | 0.79 | 1/2.1 |
| | | 2 | 5.2 | 0.82 | 1/2.6 |
| | | 2 | 7 | 0.87 | 1/3.5 |
| | | 2 | 8.8 | 0.93 | 1/4.4 |
| | 48 hour | 3 | — | — | — |
| | | — | 42 | — | — |
| | | 1 | 8.8 | 0.54 | 1/8.8 |
| | | 1 | 16 | 0.71 | 1/16 |
| | | 1 | 24 | 0.9 | 1/24 |
| | | 2 | 8.8 | 0.88 | 1/4.4 |
| | | 2 | 5 | 0.77 | 1/2.5 |
| | | 2 | 16 | 1.05 | 1/8 |
| | | 2 | 5.2 | 0.79 | 1/2.6 |
| | | 2 | 7 | 0.83 | 1/3.5 |
| | | 2 | 5.2 | 0.79 | 1/2.6 |
| | | 2 | 8.8 | 0.88 | 1/4.4 |
| *C. albicans* ATCC # 10231 | 24 hour | 15 | — | — | — |
| | | — | 4.2 | — | — |
| | | 5 | 1.6 | 0.71 | 1/0.32 |
| | | 5 | 2.4 | 0.9 | 1/0.48 |
| | | 10 | 1.6 | 1.05 | 1/1.6 |
| | 48 hour | 15 | — | — | — |
| | | — | 4.2 | — | — |
| | | 5 | 2.4 | 0.9 | 1/0.48 |

| Ca = Component A (DCOIT) Cb = Component B (Cu-tebuconazole complex) Ratio = Ca/Cb | | | | | |
|---|---|---|---|---|---|
| Test Organisms | Contact Time | Ca | Cb | S.I. | Ca/Cb |
| *Ps. Aeruginosa* ATCC # 9027 | 24 hour | 3.2 | — | — | — |
| | | — | 150 | — | — |
| | | 1.8 | 25 | 0.73 | 1/13.9 |
| | | 0.32 | 100 | 0.77 | 1/313 |
| | | 0.39 | 100 | 0.79 | 1/256 |
| | | 0.66 | 100 | 0.87 | 1/152 |
| | | 1.2 | 100 | 1.04 | 1/83 |
| | 48 hour | 5.3 | — | — | — |
| | | — | 200 | — | — |
| | | 1.8 | 25 | 0.46 | 1/13.9 |
| | | 3.2 | 25 | 0.73 | 1/7.8 |
| | | 3.9 | 25 | 0.86 | 1/6.4 |
| | | 1.8 | 50 | 0.59 | 1/27.8 |
| | | 1.8 | 100 | 0.84 | 1/55.6 |
| | | 1.8 | 150 | 1.09 | 1/83.3 |
| | | 0.39 | 100 | 0.57 | 1/256.4 |
| | | 0.66 | 100 | 0.62 | 1/151.5 |
| | | 1.2 | 100 | 0.73 | 1/83.3 |
| | | 1.8 | 100 | 0.84 | 1/55.6 |
| | | 0.53 | 150 | 0.85 | 1/283 |
| | | 1.2 | 100 | 0.73 | 1/83.3 |
| | | 1.8 | 100 | 0.84 | 1/55.6 |
| *S. aureus* | 24 hour | 0.1 | — | — | — |
| | | — | 40 | — | — |
| | | 0.02 | 35 | 0.79 | 1/1750 |
| *A. niger* ATCC # 16404 | 3 days | 1.5 | — | — | — |
| | | — | 80 | — | — |
| | | 0.44 | 40 | 0.79 | 1/90.9 |
| | | 0.55 | 40 | 0.87 | 1/72.7 |
| | | 0.44 | 50 | 0.92 | 1/113.6 |
| | | 0.4 | 60 | 1.04 | 1/150 |
| | | 0.33 | 60 | 0.97 | 1/181.8 |
| | 7 days | 2.1 | — | — | — |
| | | — | 80 | — | — |
| | | 0.55 | 40 | 0.76 | 1/72.7 |
| | | 1 | 40 | 0.98 | 1/40 |
| | | 0.55 | 50 | 0.89 | 1/90.9 |
| | | 0.55 | 60 | 1.01 | 1/109 |
| | | 0.5 | 50 | 0.88 | 1/100 |

| | Ca = Component A (copper 8-hydroxyquinoline) Cb = Component B (Cu-tebuconazole complex) Ratio = Ca/Cb | | | | |
|---|---|---|---|---|---|
| Test Organisms | Contact Time | Ca | Cb | S.I. | Ca/Cb |
| *Ps. aureginosa* ATCC # 9027 | 24 hour | 7 | — | — | — |
| | | — | 195 | — | — |
| | | 4 | 60 | 0.88 | 1/15 |
| | | 5 | 60 | 1.02 | 1/12 |
| *S. aureus* ATCC # 6538 | 24 hour | 4 | — | — | — |
| | | — | 44 | — | — |
| | 48 hour | 2 | 21 | 0.98 | 1/10.5 |
| | | 4 | — | — | — |
| | | — | 44 | — | — |
| | | 1 | 26 | 0.84 | 1/26 |
| | | 1 | 33 | 1 | 1/33 |
| | | 2 | 26 | 1.09 | 1/13 |

| | Ca = Component A (copper 8-hydroxyquinoline) Cb = Component B (DCOIT) Ratio = Ca/Cb | | | | |
|---|---|---|---|---|---|
| Test Organisms | Contact Time | Ca | Cb | S.I. | Ca/Cb |
| *Ps. aureginosa* ATCC # 9027 | 24 hour | 7 | — | — | — |
| | | — | 3.2 | — | — |
| | | 3 | 1.8 | 1 | 1/0.6 |
| | 48 hour | 7 | — | — | — |
| | | — | 5.3 | — | — |
| | | 2 | 3.9 | 1.02 | 1/2 |
| *S. aureus* ATCC # 6538 | 24 hour | 3 | — | — | — |
| | | — | 0.1 | — | — |
| | | 2 | 0.01 | 0.8 | 1/0.005 |
| | | 1 | 0.03 | 0.6 | 1/0.03 |
| | | 2 | 0.03 | 1 | 1/0.015 |

| | Ca = Component A (tebuconazole) Cb = Component B (copper 8-hydroxyquinoline) Ratio = Ca/Cb | | | | |
|---|---|---|---|---|---|
| Test Organisms | Contact Time | Ca | Cb | S.I. | Ca/Cb |
| *Ps. Aeruginosa* ATCC # 9027 | 24 hour | 900 | — | — | — |
| | | — | 7 | — | — |
| | | 200 | 2 | 1.06 | 1/0.01 |
| *S. aureus* | 24 hour | 50 | — | — | — |
| | | — | 3.3 | — | — |
| | | 40 | 0.3 | 0.89 | 1/0.008 |
| | | 30 | 0.4 | 0.72 | 1/0.01 |
| | | 20 | 0.4 | 0.52 | 1/0.02 |
| | | 50 | 0.3 | 1.09 | 1/0.06 |
| | | 40 | 0.4 | 0.92 | 1/0.01 |
| | 48 hour | 50 | — | — | — |
| | | — | 4.4 | — | — |
| | | 40 | 0.6 | 0.94 | 1/0.015 |
| | | 30 | 1 | 0.83 | 1/0.033 |
| | | 20 | 1 | 0.63 | 1/0.05 |
| | | 40 | 1 | 1.03 | 1/0.025 |
| *C. albicans* ATCC # 10231 | 24 hour | 60 | — | — | — |
| | | — | 15.8 | — | — |
| | | 50 | 0.3 | 0.85 | 1/0.006 |
| | | 50 | 0.6 | 0.87 | 1/0.012 |
| | | 50 | 1.3 | 0.92 | 1/0.026 |
| | | 50 | 1.6 | 0.93 | 1/0.032 |
| | | 50 | 2 | 0.96 | 1/0.04 |
| | | 50 | 2.6 | 1 | 1/0.052 |
| | | 50 | 3.3 | 1.04 | 1/0.066 |
| | | 40 | 0.3 | 0.69 | 1/0.008 |
| | | 40 | 0.6 | 0.7 | 1/0.015 |
| | | 40 | 0.9 | 0.72 | 1/0.023 |
| | | 40 | 1.3 | 0.75 | 1/0.033 |
| | | 40 | 1.6 | 0.77 | 1/0.04 |
| | | 40 | 2 | 0.79 | 1/0.05 |
| | | 40 | 2.6 | 0.83 | 1/0.065 |
| | | 40 | 3.3 | 0.88 | 1/0.083 |
| | | 40 | 6 | 1.05 | 1/0.15 |
| | | 30 | 0.6 | 0.54 | 1/0.02 |
| | | 30 | 0.9 | 0.56 | 1/0.03 |
| | | 30 | 1.3 | 0.58 | 1/0.043 |
| | | 30 | 1.6 | 0.6 | 1/0.053 |
| | | 30 | 2 | 0.63 | 1/0.067 |
| | | 30 | 2.6 | 0.66 | 1/0.087 |
| | | 30 | 3.3 | 0.71 | 1/0.11 |
| | | 30 | 6 | 0.88 | 1/0.2 |
| | | 30 | 9 | 1.07 | 1/0.3 |
| | | 20 | 1.3 | 0.42 | 1/0.065 |
| | | 20 | 1.6 | 0.43 | 1/0.08 |
| | | 20 | 2 | 0.46 | 1/0.1 |
| | | 20 | 2.6 | 0.5 | 1/0.13 |
| | | 20 | 3.3 | 0.54 | 1/0.165 |
| | | 20 | 6 | 0.71 | 1/0.3 |
| | | 20 | 9 | 0.9 | 1/0.45 |
| | | 10 | 3.3 | 0.38 | 1/0.33 |
| | | 10 | 6 | 0.54 | 1/0.6 |
| | | 10 | 9 | 0.74 | 1/0.9 |
| | | 10 | 12.8 | 0.98 | 1/1.28 |
| | 48 hour | 60 | — | — | — |
| | | — | 19.5 | — | — |
| | | 50 | 0.6 | 0.86 | 1/0.012 |
| | | 50 | 0.9 | 0.88 | 1/0.018 |
| | | 50 | 1.3 | 0.9 | 1/0.026 |
| | | 50 | 1.6 | 0.92 | 1/0.032 |
| | | 50 | 2 | 0.94 | 1/0.04 |
| | | 50 | 2.6 | 0.97 | 1/0.052 |
| | | 50 | 3.3 | 1 | 1/0.066 |
| | | 40 | 0.6 | 0.7 | 1/0.015 |
| | | 40 | 0.9 | 0.71 | 1/0.023 |
| | | 40 | 1.3 | 0.73 | 1/0.033 |
| | | 40 | 1.6 | 0.75 | 1/0.04 |
| | | 40 | 2 | 0.77 | 1/0.05 |
| | | 40 | 2.6 | 0.8 | 1/0.065 |
| | | 40 | 3.3 | 0.84 | 1/0.083 |
| | | 40 | 6 | 0.97 | 1/0.15 |
| | | 30 | 2 | 0.6 | 1/0.067 |
| | | 30 | 2.6 | 0.63 | 1/0.087 |
| | | 30 | 3.3 | 0.67 | 1/0.11 |
| | | 30 | 6 | 0.81 | 1/0.2 |
| | | 30 | 9 | 0.96 | 1/0.3 |
| | | 20 | 3.3 | 0.5 | 1/0.165 |
| | | 20 | 6 | 0.64 | 1/0.3 |
| | | 20 | 9 | 0.79 | 1/0.45 |
| | | 20 | 12.8 | 0.99 | 1/0.64 |
| | | 10 | 6 | 0.47 | 1/0.6 |
| | | 10 | 9 | 0.63 | 1/0.9 |
| | | 10 | 12.8 | 0.82 | 1/1.28 |
| | | 10 | 15.8 | 0.98 | 1/1.58 |
| *A. niger* ATCC # 16404 | 3 days | 8 | — | — | — |
| | | — | 6 | — | — |
| | | 7 | 0.36 | 0.94 | 1/0.05 |
| | | 7 | 0.51 | 0.96 | 1/0.07 |
| | | 7 | 0.63 | 0.98 | 1/0.09 |
| | | 7 | 0.78 | 1.01 | 1/0.11 |
| | | 6 | 0.36 | 0.81 | 1/0.06 |
| | | 6 | 0.51 | 0.84 | 1/0.085 |
| | | 6 | 0.63 | 0.86 | 1/0.105 |
| | | 6 | 0.78 | 0.88 | 1/0.13 |
| | | 6 | 1.05 | 0.93 | 1/0.175 |
| | | 6 | 1.32 | 0.97 | 1/0.22 |
| | | 6 | 2 | 1.08 | 1/0.33 |
| | | 5 | 0.78 | 0.76 | 1/0.156 |
| | | 5 | 1.05 | 0.8 | 1/0.21 |
| | | 5 | 1.32 | 0.85 | 1/0.264 |
| | | 5 | 2 | 0.96 | 1/0.4 |
| | | 4 | 0.78 | 0.63 | 1/0.195 |

-continued

Ca = Component A (tebuconazole)
Cb = Component B (copper 8-hydroxyquinoline)
Ratio = Ca/Cb

| Test Organisms | Contact Time | Ca | Cb | S.I. | Ca/Cb |
|---|---|---|---|---|---|
| | | 4 | 1.05 | 0.68 | 1/0.263 |
| | | 4 | 1.32 | 0.72 | 1/0.33 |
| | | 4 | 2 | 0.83 | 1/0.5 |
| | | 3 | 2 | 0.71 | 1/0.67 |
| | | 3 | 4 | 1.04 | 1/1.33 |
| | | 2 | 2 | 0.58 | 1/1 |
| | | 2 | 4 | 0.92 | 1/2 |
| | 7 days | 8 | — | — | — |
| | | — | 6 | — | — |
| | | 7 | 0.36 | 0.94 | 1/0.051 |
| | | 7 | 0.51 | 0.96 | 1/0.073 |
| | | 7 | 0.63 | 0.98 | 1/0.09 |
| | | 7 | 0.78 | 1.01 | 1/0.11 |
| | | 6 | 0.36 | 0.81 | 1/0.06 |
| | | 6 | 0.51 | 0.84 | 1/0.085 |
| | | 6 | 0.63 | 0.86 | 1/0.105 |
| | | 6 | 0.78 | 0.88 | 1/0.13 |
| | | 6 | 1.05 | 0.93 | 1/0.175 |
| | | 6 | 1.32 | 0.97 | 1/0.22 |
| | | 5 | 0.78 | 0.755 | 1/0.156 |
| | | 5 | 1.05 | 0.8 | 1/0.21 |
| | | 5 | 1.32 | 0.845 | 1/0.264 |
| | | 5 | 2 | 0.96 | 1/0.4 |
| | | 4 | 0.78 | 0.63 | 1/0.195 |
| | | 4 | 1.05 | 0.68 | 1/0.263 |
| | | 4 | 1.32 | 0.72 | 1/0.33 |
| | | 4 | 2 | 0.83 | 1/0.5 |
| | | 3 | 2 | 0.71 | 1/0.67 |
| | | 3 | 4 | 1.04 | 1/1.33 |
| | | 2 | 4 | 0.92 | 1/2 |

TABLE 10

Ca = Component A (tebuconazole)
Cb = Component B (DCOIT)
Ratio = Ca/Cb

| Test Organisms | Contact Time | Ca | Cb | S.I. | Ca/Cb |
|---|---|---|---|---|---|
| Ps. Aeruginosa ATCC # 9027 | 48 hour | 900 | — | — | — |
| | | — | 3.9 | — | — |
| | | 50 | 2.6 | 0.72 | 1/0.052 |
| | | 100 | 2.6 | 0.78 | 1/0.026 |
| | | 200 | 2.6 | 0.89 | 1/0.013 |
| | | 300 | 1.8 | 0.79 | 1/0.006 |
| | | 400 | 1.8 | 0.91 | 1/0.005 |
| | | 500 | 1.8 | 1.02 | 1/0.004 |
| S. aureus | 24 hour | 50 | — | — | — |
| | | — | 0.2 | — | — |
| | | 40 | 0.01 | 0.85 | 1/0.0003 |
| | | 30 | 0.02 | 0.7 | 1/0.0007 |
| | | 40 | 0.02 | 0.9 | 1/0.0005 |
| | | 40 | 0.03 | 0.95 | 1/0.0008 |
| | | 40 | 0.04 | 1 | 1/0.001 |
| | 48 hour | 50 | — | — | — |
| | | — | 0.3 | — | — |
| | | 40 | 0.04 | 0.93 | 1/0.001 |
| | | 30 | 0.1 | 0.93 | 1/0.003 |
| A. niger ATCC # 16404 | 3 days | 8 | — | — | — |
| | | — | 1.8 | — | — |
| | | 6 | 0.32 | 0.93 | 1/0.053 |
| | | 6 | 0.39 | 0.97 | 1/0.065 |
| | | 5 | 0.32 | 0.8 | 1/0.064 |
| | | 5 | 0.39 | 0.84 | 1/0.078 |
| | | 5 | 0.53 | 0.92 | 1/0.106 |
| | | 5 | 0.66 | 0.99 | 1/0.132 |
| | | 4 | 0.32 | 0.68 | 1/0.08 |
| | | 4 | 0.39 | 0.72 | 1/0.098 |
| | | 4 | 0.53 | 0.79 | 1/0.133 |
| | | 4 | 0.66 | 0.87 | 1/0.165 |
| | | 3 | 0.39 | 0.59 | 1/0.13 |
| | | 3 | 0.53 | 0.67 | 1/0.177 |
| | | 3 | 0.66 | 0.74 | 1/0.22 |
| | | 3 | 1.2 | 1.04 | 1/0.4 |
| | | 2 | 1.2 | 0.92 | 1/0.6 |
| | 7 days | 8 | — | — | — |
| | | — | 3.2 | — | — |
| | | 7 | 0.32 | 0.98 | 1/0.046 |
| | | 6 | 0.39 | 0.87 | 1/0.065 |
| | | 6 | 0.53 | 0.92 | 1/0.088 |
| | | 6 | 0.66 | 0.96 | 1/0.11 |
| | | 5 | 0.53 | 0.79 | 1/0.106 |
| | | 5 | 0.39 | 0.75 | 1/0.078 |
| | | 5 | 0.53 | 0.79 | 1/0.106 |
| | | 5 | 0.66 | 0.83 | 1/0.132 |
| | | 4 | 0.53 | 0.67 | 1/0.133 |
| | | 4 | 0.66 | 0.71 | 1/0.165 |
| | | 4 | 1.2 | 0.88 | 1/0.3 |

Ca = Component A (tebuconazole)
Cb = Component B (OIT)
Ratio = Ca/Cb

| Test Organisms | Contact Time | Ca | Cb | S.I. | Ca/Cb |
|---|---|---|---|---|---|
| Ps. Aeruginosa ATCC # 9027 | 24 hour | 900 | — | — | — |
| | | — | 390 | — | — |
| | | 800 | 66 | 1.06 | 1/0.083 |
| | | 700 | 120 | 1.09 | 1/0.17 |
| | | 600 | 120 | 0.97 | 1/0.2 |
| | | 500 | 120 | 0.86 | 1/0.24 |
| | 48 hour | 900 | — | — | — |
| | | — | 390 | — | — |
| | | 500 | 180 | 1.02 | 1/0.36 |
| S. aureus | 24 hour | 50 | — | — | — |
| | | — | 63 | — | — |
| | | 10 | 51 | 1.01 | 1/5.1 |
| C. albicans ATCC # 10231 | 24 hour | 50 | — | — | — |
| | | — | 0.9 | — | — |
| | | 40 | 0.02 | 0.82 | 1/0.005 |
| | | 40 | 0.026 | 0.83 | 1/0.0007 |
| | | 40 | 0.033 | 0.84 | 1/0.0008 |
| | | 40 | 0.06 | 0.87 | 1/0.015 |
| | | 40 | 0.09 | 0.90 | 1/0.0023 |
| | | 40 | 0.13 | 0.94 | 1/0.0033 |
| | | 40 | 0.16 | 0.98 | 1/0.004 |
| | | 30 | 0.06 | 0.67 | 1/0.002 |
| | | 30 | 0.09 | 0.70 | 1/0.003 |
| | | 30 | 0.13 | 0.74 | 1/0.004 |
| | | 30 | 0.16 | 0.78 | 1/0.005 |
| | | 30 | 0.2 | 0.82 | 1/0.0067 |
| | | 30 | 0.26 | 0.89 | 1/0.0087 |
| | | 30 | 0.33 | 0.97 | 1/0.011 |
| | | 20 | 0.33 | 0.77 | 1/0.0165 |

Ca = Component A (tebuconazole)
Cb = Component B (CMIT/MIT)
Ratio = Ca/Cb

| Test Organisms | Contact Time | Ca | Cb | S.I. | Ca/Cb |
|---|---|---|---|---|---|
| S. aureus | 24 hour | 50 | — | — | — |
| | | — | 1 | — | — |
| | | 40 | 0.04 | 0.84 | 1/0.001 |
| | | 30 | 0.06 | 0.66 | 1/0.002 |
| | | 20 | 0.1 | 0.5 | 1/0.005 |

| | Ca = Component A (tebuconazole) Cb = Component B (CMIT/MIT) Ratio = Ca/Cb | | | | |
|---|---|---|---|---|---|
| Test Organisms | Contact Time | Ca | Cb | S.I. | Ca/Cb |
| | | 10 | 0.27 | 0.47 | 1/0.027 |
| | | 10 | 0.33 | 0.53 | 1/0.033 |
| | | 10 | 0.44 | 0.64 | 1/0.044 |
| | | 10 | 0.55 | 0.75 | 1/0.055 |
| | | 20 | 0.15 | 0.55 | 1/0.008 |
| | | 20 | 0.21 | 0.61 | 1/0.011 |
| | | 20 | 0.26 | 0.66 | 1/0.013 |
| | | 20 | 0.32 | 0.72 | 1/0.016 |
| | | 20 | 0.44 | 0.84 | 1/0.022 |
| | | 20 | 0.55 | 0.95 | 1/0.028 |
| | | 20 | 0.21 | 0.61 | 1/0.011 |
| | | 30 | 0.1 | 0.7 | 1/0.003 |
| | | 30 | 0.15 | 0.75 | 1/0.005 |
| | | 30 | 0.21 | 0.81 | 1/0.007 |
| | | 30 | 0.26 | 0.86 | 1/0.008 |
| | | 30 | 0.32 | 0.92 | 1/0.011 |
| | | 30 | 0.44 | 1.04 | 1/0.015 |
| | | 40 | 0.06 | 0.86 | 1/0.002 |
| | | 40 | 0.1 | 0.9 | 1/0.003 |
| | | 40 | 0.15 | 0.95 | 1/0.004 |
| | | 40 | 0.21 | 1.01 | 1/0.005 |
| | | 40 | 0.26 | 1.06 | 1/0.007 |
| | 48 hour | 50 | — | — | — |
| | | — | 3 | — | — |
| | | 40 | 0.1 | 0.83 | 1/0.003 |
| | | 40 | 0.15 | 0.85 | 1/0.004 |
| | | 40 | 0.21 | 0.87 | 1/0.005 |
| | | 40 | 0.26 | 0.89 | 1/0.007 |
| | | 40 | 0.33 | 0.91 | 1/0.008 |
| | | 40 | 0.55 | 0.98 | 1/0.014 |
| | | 30 | 0.33 | 0.71 | 1/0.011 |
| | | 30 | 0.55 | 0.78 | 1/0.018 |
| | | 30 | 1 | 0.93 | 1/0.033 |
| | | 20 | 1 | 0.73 | 1/0.05 |
| | | 20 | 2 | 1.07 | 1/0.1 |
| C. albicans ATCC # 10231 | 24 hour | 50 | — | — | — |
| | | — | 2.1 | — | — |
| | | 40 | 0.1 | 0.85 | 1/0.0025 |
| | | 40 | 0.15 | 0.87 | 1/0.0038 |
| | | 40 | 0.21 | 0.90 | 1/0.0053 |
| | | 40 | 0.26 | 0.92 | 1/0.0065 |
| | | 40 | 0.33 | 0.96 | 1/0.0083 |
| | | 30 | 0.15 | 0.67 | 1/0.005 |
| | | 30 | 0.21 | 0.70 | 1/0.007 |
| | | 30 | 0.26 | 0.72 | 1/0.0087 |
| | | 30 | 0.33 | 0.76 | 1/0.011 |
| | | 30 | 0.44 | 0.81 | 1/0.015 |
| | | 30 | 0.55 | 0.86 | 1/0.018 |
| | | 20 | 0.55 | 0.66 | 1/0.028 |
| | | 20 | 1 | 0.88 | 1/0.05 |
| | | 10 | 1.5 | 0.91 | 1/0.15 |
| | 48 hour | 50 | — | — | — |
| | | — | 2.6 | — | — |
| | | 30 | 0.55 | 0.81 | 1/0.018 |
| | | 30 | 1 | 0.98 | 1/0.033 |
| | | 20 | 1.5 | 0.98 | 1/0.075 |

| | Ca = Component A (propiconazole) Cb = Component B (copper 8-hydroxyquinoline) Ratio = Ca/Cb | | | | |
|---|---|---|---|---|---|
| Test Organisms | Contact Time | Ca | Cb | S.I. | Ca/Cb |
| S. aureus | 24 hour | 100 | — | — | — |
| | | — | 3.3 | — | — |
| | | 90 | 0.6 | 1.08 | 1/0.007 |
| | | 70 | 1 | 1 | 1/0.014 |
| | | 60 | 1.5 | 1.05 | 1/0.025 |
| | | 50 | 1.5 | 0.95 | 1/0.03 |
| | | 40 | 2.1 | 1.04 | 1/0.053 |
| | 48 hour | 100 | — | — | — |
| | | — | 3.3 | — | — |
| | | 90 | 0.6 | 1.08 | 1/0.007 |
| C. albicans ATCC # 10231 | 24 hour | 50 | — | — | — |
| | | — | 19.5 | — | — |
| | | 40 | 0.9 | 0.85 | 1/0.023 |
| | | 40 | 1.3 | 0.87 | 1/0.033 |
| | | 40 | 1.6 | 0.88 | 1/0.04 |
| | | 40 | 2 | 0.90 | 1/0.05 |
| | | 40 | 2.6 | 0.93 | 1/0.065 |
| | | 40 | 3.3 | 0.97 | 1/0.083 |
| | | 30 | 2.6 | 0.73 | 1/0.087 |
| | | 30 | 3.3 | 0.77 | 1/0.11 |
| | | 30 | 6 | 0.91 | 1/0.2 |
| | | 20 | 9 | 0.86 | 1/0.45 |
| | | 20 | 12.8 | 1.06 | 1/0.64 |
| | | 10 | 9 | 0.66 | 1/0.9 |
| | | 10 | 12.8 | 0.86 | 1/1.28 |
| | 48 hour | 50 | — | — | — |
| | | — | 19.5 | — | — |
| | | 40 | 1.3 | 0.87 | 1/0.033 |
| | | 40 | 1.6 | 0.88 | 1/0.04 |
| | | 40 | 2 | 0.90 | 1/0.05 |
| | | 40 | 2.6 | 0.93 | 1/0.065 |
| | | 40 | 3.3 | 0.97 | 1/0.083 |
| | | 30 | 2.6 | 0.73 | 1/0.087 |
| | | 30 | 3.3 | 0.77 | 1/0.11 |
| | | 30 | 6 | 0.91 | 1/0.2 |
| A. niger ATCC # 16404 | 3 days | 20 | — | — | — |
| | | — | 6 | — | — |
| | | 15 | 1.3 | 0.97 | 1/0.087 |
| | | 10 | 2 | 0.83 | 1/0.2 |
| | 7 days | 25 | — | — | — |
| | | — | 6 | — | — |
| | | 15 | 2 | 0.93 | 1/0.93 |

| | Ca = Component A (propiconazole) Cb = Component B (DCOIT) Ratio = Ca/Cb | | | | |
|---|---|---|---|---|---|
| Test Organisms | Contact Time | Ca | Cb | S.I. | Ca/Cb |
| S. aureus | 24 hour | 100 | — | — | — |
| | | — | 0.2 | — | — |
| | | 90 | 0.2 | 1 | 1/0.002 |
| | | 90 | 0.03 | 1.05 | 1/0.003 |
| A. niger ATCC # 16404 | 3 days | 20 | — | — | — |
| | | — | 2.6 | — | — |
| | | 15 | 0.39 | 0.90 | 1/0.026 |
| | | 15 | 0.53 | 0.95 | 1/0.035 |
| | | 10 | 0.66 | 0.75 | 1/0.066 |
| | | 10 | 1.2 | 0.96 | 1/0.12 |
| | | 5 | 1.8 | 0.94 | 1/0.36 |
| | 7 days | 20 | — | — | — |
| | | — | 3.2 | — | — |
| | | 10 | 1.2 | 0.88 | 1/0.875 |

| | Ca = Component A (propiconazole) Cb = Component B (OIT) Ratio = Ca/Cb | | | | |
|---|---|---|---|---|---|
| Test Organisms | Contact Time | Ca | Cb | S.I. | Ca/Cb |
| Ps. Aeruginosa ATCC # 9027 | 24 hour | 800 | — | — | — |
| | | — | 390 | — | — |

-continued

| Test Organisms | Contact Time | Ca | Cb | S.I. | Ca/Cb |
|---|---|---|---|---|---|
| | | 500 | 180 | 1.09 | 1/0.36 |
| | 48 hour | 800 | — | — | — |
| | | — | 525 | — | — |
| | | 600 | 180 | 1.09 | 1/0.3 |
| S. aureus | 24 hour | 100 | — | — | — |
| | | — | 63 | — | — |
| | | 90 | 0.4 | 0.91 | 1/0.004 |
| | | 80 | 0.6 | 0.81 | 1/0.008 |
| | | 70 | 2.4 | 0.74 | 1/0.034 |
| | | 60 | 2.4 | 0.64 | 1/0.04 |
| | | 50 | 13 | 0.71 | 1/0.26 |
| | | 50 | 24 | 0.88 | 1/0.48 |
| | | 50 | 36 | 1.07 | 1/0.72 |
| | | 60 | 24 | 0.98 | 1/0.4 |
| | | 70 | 10.5 | 0.87 | 1/0.25 |
| | | 70 | 13.2 | 0.91 | 1/0.19 |
| | | 70 | 24 | 1.08 | 1/0.34 |
| | | 80 | 13.2 | 1.01 | 1/0.167 |
| | | 90 | 10.5 | 1.07 | 1/0.12 |
| | 48 hour | 100 | — | — | — |
| | | — | 78 | — | — |
| | | 90 | 0.8 | 0.91 | 1/0.009 |
| | | 80 | 1.1 | 0.81 | 1/0.014 |
| | | 70 | 6.3 | 0.78 | 1/0.09 |
| | | 60 | 7.8 | 0.7 | 1/0.13 |
| | | 50 | 13 | 0.67 | 1/0.26 |
| | | 40 | 51 | 1.05 | 1/1.28 |
| | | 50 | 36 | 0.96 | 1/0.72 |
| | | 60 | 24 | 0.91 | 1/0.4 |
| | | 60 | 36 | 1.06 | 1/0.6 |
| | | 70 | 24 | 1.01 | 1/0.34 |
| | | 80 | 13 | 0.97 | 1/0.16 |
| | | 90 | 13 | 1.07 | 1/0.14 |
| | | 90 | 10.5 | 1.03 | 1/0.12 |
| C. albicans ATCC # 10231 | 24 hour | 50 | — | — | — |
| | | — | 1.3 | — | — |
| | | 40 | 0.06 | 0.85 | 1/0.0015 |
| | | 30 | 0.06 | 0.65 | 1/0.002 |
| | | 20 | 0.33 | 0.65 | 1/0.0165 |
| | | 10 | 0.6 | 0.66 | 1/0.06 |
| | | 40 | 0.09 | 0.87 | 1/0.0023 |
| | | 40 | 0.13 | 0.90 | 1/0.0033 |
| | | 40 | 0.16 | 0.92 | 1/0.004 |
| | | 40 | 0.2 | 0.95 | 1/0.005 |
| | | 30 | 0.09 | 0.67 | 1/0.003 |
| | | 30 | 0.13 | 0.70 | 1/0.004 |
| | | 30 | 0.16 | 0.72 | 1/0.005 |
| | | 30 | 0.2 | 0.75 | 1/0.007 |
| | | 30 | 0.26 | 0.80 | 1/0.009 |
| | | 30 | 0.33 | 0.85 | 1/0.011 |
| | | 20 | 0.6 | 0.86 | 1/0.03 |
| | | 10 | 0.9 | 0.89 | 1/0.09 |
| | 48 hour | 50 | — | — | — |
| | | — | 1.3 | — | — |
| | | 40 | 0.09 | 0.87 | 1/0.0023 |
| | | 20 | 0.6 | 0.86 | 1/0.03 |
| | | 40 | 0.13 | 0.90 | 1/0.003 |
| | | 40 | 0.16 | 0.92 | 1/0.004 |
| | | 40 | 0.2 | 0.95 | 1/0.005 |

Ca = Component A (propiconazole)
Cb = Component B (CMIT/MIT)
Ratio = Ca/Cb

| Test Organisms | Contact Time | Ca | Cb | S.I. | Ca/Cb |
|---|---|---|---|---|---|
| S. aureus | 24 hour | 100 | — | — | — |
| | | — | 1 | — | — |
| | | 60 | 0.44 | 1.04 | 1/0.007 |
| | | 50 | 0.44 | 0.94 | 1/0.009 |
| | | 40 | 0.44 | 0.84 | 1/0.011 |
| | | 40 | 0.55 | 0.95 | 1/0.014 |
| | | 50 | 0.55 | 1.05 | 1/0.011 |
| C. albicans ATCC # 10231 | 24 hour | 50 | — | — | — |
| | | — | 2.6 | — | — |
| | | 40 | 0.44 | 0.97 | 1/0.011 |
| | | 30 | 1 | 0.98 | 1/0.033 |
| | | 20 | 1.5 | 0.98 | 1/0.075 |
| A. niger ATCC # 16404 | 3 days | 20 | — | — | — |
| | | — | 2.6 | — | — |
| | | 15 | 0.4 | 0.90 | 1/0.027 |
| | | 10 | 1.2 | 0.96 | 1/0.12 |

Ca = Component A (propiconazole)
Cb = Component B (IPBC)
Ratio = Ca/Cb

| Test Organisms | Contact Time | Ca | Cb | S.I. | Ca/Cb |
|---|---|---|---|---|---|
| A. niger ATCC # 16404 | 3 days | 20 | — | — | — |
| | | — | 0.4 | — | — |
| | | 15 | 0.01 | 0.78 | 1/0.0007 |
| | | 15 | 0.02 | 0.80 | 1/0.0013 |
| | | 15 | 0.03 | 0.83 | 1/0.002 |
| | | 15 | 0.04 | 0.85 | 1/0.0027 |
| | | 15 | 0.05 | 0.88 | 1/0.0033 |
| | | 15 | 0.07 | 0.93 | 1/0.0047 |
| | | 15 | 0.09 | 0.98 | 1/0.006 |
| | | 10 | 0.11 | 0.78 | 1/0.011 |

Ca = Component A (DCOIT)
Cb = Component B (thifluzamide)
Ratio = Ca/Cb

| Test Organisms | Contact Time | Ca | Cb | S.I. | Ca/Cb |
|---|---|---|---|---|---|
| G. trabeum ATCC # 11539 | 4 weeks | 320 | — | — | — |
| | | — | >960 | — | — |
| | | 80 | 80 | <0.33 | 1/1 |
| T. vesicolor ATCC # 42462 | 4 weeks | 320 | — | — | — |
| | | — | 320 | — | — |
| | | 80 | 80 | 0.5 | 1/1 |

The invention claimed is:
1. A synergistic antimicrobial composition comprising:
(a) 4,5-dichloro-2-n-octyl-4-isothiazolin-3-one; and
(b) copper tebuconazole; wherein a weight ratio of 4,5-dichloro-2-n-octyl-4-isothiazolin-3-one to copper tebuconazole is from 1:333 to 1:6.3.

* * * * *